United States Patent [19]

Adams et al.

[11] Patent Number: 4,986,917

[45] Date of Patent: Jan. 22, 1991

[54] SELECTIVE RECOVERY OF A NITROPHENOLIC BY-PRODUCT FROM NITRATION WASTE WATER BY EXTRACTION

[75] Inventors: Earl G. Adams, Grand Bay, Ala.; Arthur C. Bayer, Ocean Springs, Miss.; Alan D. Farmer, Biloxi, Miss.; Brenda J. Hook, Gautier, Miss.

[73] Assignee: First Chemical Corporation, Pascagoula, Miss.

[21] Appl. No.: 377,048

[22] Filed: Jul. 10, 1989

[51] Int. Cl.$^5$ .............................................. C02F 1/26
[52] U.S. Cl. ..................................... 210/634; 210/909
[58] Field of Search ................ 568/757, 749; 210/726, 210/634, 909, 710, 712, 724

[56] References Cited

U.S. PATENT DOCUMENTS 4,418,221  11/1983  Yasuda et al. .................. 568/749 X
4,597,875   7/1986  Carr et al. ....................... 210/726 X Primary Examiner—Frank Spear
Attorney, Agent, or Firm—A. W. Breiner

[57] ABSTRACT

A process for selectively recovering a nitrophenolic by-product from nitration waste water in substantially pure form by solvent extraction is provided. The pH of the waste water is adjusted using an acid to affect the solubility of a particular nitrophenolic by-product in the waste water so that the by-product is selectively separable from the other components of the nitration waste water by solvent extraction.

17 Claims, No Drawings

SELECTIVE RECOVERY OF A NITROPHENOLIC BY-PRODUCT FROM NITRATION WASTE WATER BY EXTRACTION

RELATED APPLICATIONS

The present application is related to (1) an earlier filed application entitled "Process For Extracting And Disposing Of Nitrophenolic By-Products", U.S. Ser. No. 07/242,882 filed Sept. 12, 1988 and (2) a concurrently filed application entitled "Selective Recovery Of Nitrophenolic By-Products From Nitration Waste Water By Precipitation" having the same inventors.

FIELD OF INVENTION

The present invention is directed to the recovery of select nitrophenolic by-products in substantially pure form from nitration waste water. In particular, the invention is directed to the selective recovery of 2,4-dinitrophenol, and picric acid from pH controlled nitration waste water by solvent extraction. The waste water pH is controlled using an acid so that the solubility of the different nitrophenolic by-products present in the water is selectively affected and accordingly, the effectiveness of the partition coefficient of the extraction to recover a by-product is affected. If the nitration waste water is contaminated with dinitrocresols the dinitrocresols can also be extracted.

BACKGROUND OF THE INVENTION

During a nitration process to produce a desired chemical product, such as nitrotoluene or nitrobenzene, nitrophenolic by-products are produced. These by-products are usually present in the form of di- and tri-nitrophenols and may also include di- and tri-nitrocresols. The by-products are separated from the desired nitrated product by washing. The by-products are then present in the wash water or waste water stream which must be disposed of in an environmentally safe manner.

There are various processes known in the art for disposing of waste water containing nitrophenolic materials. These processes, however, are directed to the disposal of the by-products and water. The by-products are indiscriminately recovered and then disposed of, such as by incineration. One suggested process for disposing of these by-products is to collect the waste water from the nitration washers in a lagoon and adjust the pH of the waste water to approximately 1.5 causing the nitrophenolic compounds present in the water to indiscriminately precipitate. Due to the environmental concerns lagooning is not a satisfactory method.

The art discloses various extraction processes in relation to separating specified compounds, including phenolic compounds from waste water. Additionally, the art recognizes the effect of a compound's partition coefficient value in an extraction process, including in the separation of a mixture of isomeric phenols. For example, U.S. Patent No. 2,807,654 discloses a process for removing phenols from an aqueous phenol solution comprising contacting the aqueous solution with an organic solvent containing an extract phase to form an organic and aqueous phase, adjusting the pH of the mixture to between 5 and 9, and extracting. The adjustment of the pH is for the purpose of neutralizing the solution. Either a mineral acid or alkaline composition can be utilized to adjust the pH depending on the initial pH of the solution.

U.S. Pat. No. 2,812,305 discloses the purification of phenol-bearing water recovered from coke plants by extraction using a solvent and 2-methyl-5-ethylpyridine. Prior to extraction, the water's pH is brought to a value of from 6.5 to 9.5 using sulfuric acid. It is disclosed that by increasing the volume of the solvent relative to the volume of the phenol-bearing water, that the effectiveness of the extraction will be increased.

U.S. Pat. No. 4,152,528 discloses the extraction of phenol from a phenol-water mixture using an aromatic hydrocarbon and a ketone as the extracting medium. The ketone is disclosed as providing an extraction medium having an improved partition coefficient.

U.S. Pat. No. 2,581,406 discloses the separation of individual isomeric phenols from a phenol mixture by countercurrent distribution using a solvent system and an alkaline buffer. When the mixture of isomeric phenols is distributed, i.e. partitioned, between a pair of immiscible solvents and the alkaline buffer, each isomer is distributed independently from the other isomer and, accordingly, is separated due to each isomer having a different partition coefficient. The alkaline buffer is used concurrently with the solvent and is disclosed as being beneficial in that the spread between the partition coefficients is increased by varying the solution pH on the alkaline side. The '406 patent refers to an article published in *Analytical Chemistry*, vol. 20, pg. 951 (1948) by Warshowsky et al as showing that phenol and m-cresol can be partly separated by a distribution in a system of two immiscible solvents wherein the heavier solvent is an acidic buffer. As in the '406 patent, however, the solvent and buffer are utilized concurrently. The article also states that the partition coefficient of the phenol was not markedly affected by the pH of the aqueous phase.

U.S. Pat. No. 4,401,570 discloses the removal of pesticidal esters from an aqueous alkaline waste stream containing the esters and other impurities. The removal encompasses acidifying the waste stream to a pH of 2.5 to 5.5 to form surface active reaction products with the organics present in the water to reduce the organics content. Extraction of the water is then performed using a hydrocarbon having from 5 to 10 carbon atoms. The extraction separates out the ester from the aqueous product.

U.S. Pat. No. 2,327,312 discloses a process for separating alkyl phenols which includes (1) sulphonating the alkyl phenols; (2) diluting the sulphonated phenols with water and, optionally, a solvent; (3) allowing the materials to hydrolyze; (4) extracting the materials with a solvent; (5) adjusting the mixture to allow for further hydrolysis of the residual mixture; (6) performing a second solvent extraction; and (7) repeating the above process under varying conditions until all of the phenolic fractions have been separated. The use of different sulphonation temperatures and rates as well as different hydrolysis conditions provide for the selective separation of the different phenolic fractions.

U.S. Pat. No. 3,966,594 discloses the treatment of waste water containing anionic substances involving the contacting of the waste water with an amine solvent, separating the aqueous and organic layers formed, and contacting the organic layer with an aqueous alkali solution to transfer the anionic substances to the alkali layer and recover the amine in the organic layer. It is noted that prior to the above process, the pH is adjusted to preferably less than 2 with an acid so that any insoluble matter produced can be filtered out before the multiple extractions.

U.S. Pat. No. 3,467,721 discloses the extraction of phenol from an aqueous phenol mixture using mesityl oxide as a solvent. It is preferred, if necessary, that the pH of the mixture is adjusted to neutral or slightly acid prior to the extraction. The mesityl oxide solvent is said to affect the partition coefficient between the solvents and water for the phenol.

The art does not disclose a process wherein the pH of nitration waste water is adjusted and controlled prior to extraction to affect the solubility of a particular nitrophenolic by-product contained among the plurality of by-products in the waste water to provide for the selective recovery of a select by-product by extraction, particularly in a substantially pure form.

The ability to selectively recover a particular nitrophenolic by-product in substantially pure form from nitration waste water utilizing an acid followed by extraction is surprising in that while the prior art discloses treating solutions with an acid prior to extraction, it is for the purpose of (1) simply neutralizing the solution, (2) reducing the content of a material which is not to be recovered, (3) affecting non-nitrophenolic compounds, and/or (4) requires additional purification steps following the extraction to obtain a particular nitrophenol in substantially pure form. A selective extraction of a particular nitrophenol from a solution containing a plurality of isomeric and nonisomeric nitrophenolic compounds based on the pH control of the solution which does not require additional purification steps following an extraction to obtain a substantially pure product is economically and environmentally important.

OBJECTS OF THE INVENTION

A primary object of the present invention is to provide a process for the selective recovery of a nitrophenolic by-product from nitration waste water through (1) the control of the nitration waste water's pH to affect the solubility of the by-product and (2) solvent extraction.

A further primary object of the present invention is to provide for the selective recovery of a nitrophenolic by-product from nitration waste water in substantially pure form so that the recovered by-product is suitable for commercial sale.

A further primary object of the present invention is to provide a process for selectively removing one or more nitrophenolic by-products from nitration waste water to place the nitration waste water in a more favorable condition for disposal.

GENERAL DESCRIPTION OF THE INVENTION

The present invention provides an economical and efficient process for selectively recovering in a substantially pure form a nitrophenolic by-product, more particularly 2,4-dinitrophenol (2,4-DNP) and picric acid, from nitration waste water containing a plurality of nitrophenolic by-products. If the waste water is contaminated with dinitrocresols, the dinitrocresols can also be selectively recovered. However, for the reasons more fully set forth below, the level of purity of the dinitrocresols obtained is not as great as that present when selectively recovering 2,4-DNP and picric acid.

The selective recovery of a nitrophenolic by-product is provided through the control of the waste water pH with an acid and solvent extraction. The nitrophenolic by-products 2,4-DNP and picric acid are recovered in substantially pure form, i.e. is suitable for commercial sale without further purification. "In substantially pure form" is understood to mean that the desired nitrophenolic by-product has at most 5% impurities (on a dry basis).

An example of a nitration process which results in the production of a waste water stream containing the nitrophenolic by-products of di- and tri-nitrophenols is the nitration of benzene with nitric acid in the presence of sulfuric acid to produce nitrobenzene and the above-named by-products. If there is external contamination of the benzene starting material with toluene, the nitration waste water will also become contaminated with dinitrocresols.

Following the nitration process, the nitrophenolic by-products are separated from the nitrated product by washing. A base, such as sodium hydroxide, is typically utilized to wash the nitrated product. The nitrated phenols are organic acids which vary in acidity from the acidity of carbonated water to being more acidic than phosphoric acid. These organic acids have a high solubility in nitrated aromatics and low solubility in water. When a base is reacted with these acids, the salt is formed which is nearly insoluble in hydrocarbon solvents and very soluble in water. By utilizing counter-current extraction, these salts can be washed from the nitrated product.

The nitration waste water which is utilized in the process of the present invention preferably has had the nitrobenzene essentially removed from the water by a previously performed extraction. The removal of the nitrobenzene can be by a single conventional extraction with toluene. This extraction does not involve any pH adjustment of the solution. A 5:1 water/toluene ratio is preferably employed. The nitrobenzene concentration is substantially reduced by the one step extraction leaving only a trace amount of nitrobenzene in the waste water.

A primary factor in selectively recovering a marketable nitrophenolic by-product from nitration waste water in substantially pure product according to the present invention is the control of the pH of the nitration waste water by adding an acid, particularly sulfuric acid, to the waste water. The pH adjustment of the nitration waste water allows for the solvent extraction of a selected nitrophenolic by-product.

The selective extraction of a particular nitrophenolic compound from a solution containing picric acid, dinitrophenols and, possibly, dinitrocresols involves first extracting the materials having a higher pKa, i.e. extracting dinitrophenol and/or dinitrocresols, depending on if one or both are present, if it is desired to obtain picric acid. This is required since the compounds will not extract into an organic solvent until the aqueous solution is at or near the pK of the solute. Accordingly, all compounds having a pKa near or above the aqueous pH will extract. By controlling the pH of the solution, it is therefore possible to determine which compound or compounds will be extracted. The pKa of 2,4-DNP and dinitrocresols are similar. Accordingly, if the nitration waste water is contaminated with dinitrocresols, some 2,4-DNP will be extracted along with the dinitrocresols. Thereafter, when the 2,4-DNP is selectively extracted, it will be present in a lesser quantity.

The designation pK is used in the conventional manner, i.e., as a measurement of the completeness of an incomplete chemical reaction. It is defined as the negative logarithm (to the base of 10) of the equilibrium constant K for the reaction in question. The pKa signifies the value where the acid and salt concentrations are equal.

The effectiveness of the extraction of a selected nitrophenolic by-product or solute from a solvent system, i.e. the nitration waste water, to a second solvent system is measured by a value called the partition coefficient. The partition coefficient is a ratio value of the initial and final concentrations of the solute in the initial solvent system. In order to increase the relative concentration of the solute in a second solvent, the solubility of the solute in its primary solvent must be decreased. The process of the present invention selectively decreases the solubility of the nitrophenolic by-product sought t be recovered in the nitration waste water by increasing the solution acidity of the nitration waste water to a particular level. More specifically, sulfuric acid is added to the nitration waste water until the pH of the waste water reaches a level which affects the solubility of the nitrophenolic by-product to be recovered.

The particular nitrophenolic by-product being recovered determines the level to which the pH of the nitration waste water is adjusted. The pH level of the waste water is allowed to stabilize prior to the extraction of the selected by-product. When 2,4-DNP is to be selectively recovered in substantially pure form from nitration waste water, the pH is adjusted to a level in the range of from about 4.5 to 2.0, preferably in the range of from 3.0 to 2.0 to obtain 2,4-DNP in its most pure condition. Thereafter, when picric acid is to be selectively recovered, the pH is adjusted to a level in the range of from about 2.0 to 0.5, preferably from about 1.2 to 0.8 to recover picric acid at its highest level of purity. If the nitration waste water is contaminated with dinitrocresols, the dinitrocresols can be recovered when the pH is adjusted to be in the range of from 4.5 to 3.7. As noted above, some 2,4-DNP will also be recovered with the dinitrocresols and, accordingly, the amount of 2,4-DNP that will be selectively recoverable thereafter from the same nitration waste water will be lesser in quantity.

More specifically, the process of the present invention is carried out by placing nitration waste water, which contains at least one of the by-products of 2,4-DNP and picric acid and has preferably had any nitrobenzene removed therefrom, in a reaction container having any conventional means of agitation. Small amounts of sulfuric acid are added to the nitration waste water with agitation until a desired pH level in the water has been reached. The pH level of the solution is monitored with a pH sensor so that the addition of the sulfuric acid can be stopped once a certain pH level, which is determined by the by-product being recovered, is reached. Once the desired solution pH is obtained, the pH is allowed to stabilize. The amount of sulfuric acid added will vary depending upon the initial pH of the waste water and the level to which the pH is adjusted.

A solvent is then added to the pH adjusted nitration waste water. The solvent is usually added in a ratio range of from about 2:1 to 8:1 of pH adjusted water/solvent, preferably a ratio of 5:1. Suitable solvents include aromatic hydrocarbons such as for example ethylbenzene, benzene and toluene; non-aromatic solvents such as hexane, methyl ethyl ketone and methyl isobutyl ketone; and chlorinated solvents. The aromatic solvents are preferred, particularly ethylbenzene, due to the low solubility of water and low cost of the solvents. Benzene is not a preferred solvent due to its toxicity and accordingly, related problems in its disposal. Likewise, chlorinated solvents are not preferred in view of their toxicity and the environmental considerations inherent with their use.

The stirring of the solution is increased to provide for a full mixing of the added solvent and the nitration waste water. The stirring is continued until the solution is fully mixed. Thereafter, the contents of the reaction container are allowed to form distinct organic and water layers which are separated, for example with a separatory funnel. The desired nitrophenolic by-product will be present in the organic layer and is recoverable by any conventional method, such as evaporation.

If a different nitrophenolic by-product is to be recovered from the same nitration waste water, the water layer recovered from the extraction is reintroduced into the reaction container which has, preferably, been rinsed with deionized water to remove any residue from the first extraction. The pH of the water is readjusted to a new (lower) pH level determined by the by-product to be recovered using the same procedure as set forth above regarding the adjustment of the waste water pH with sulfuric acid. The addition of a solvent and the separation into distinct layers is then repeated as performed in the first extraction. The apparatus utilized in the separation of the organic and water layers should preferably be rinsed with water and acetone prior to the second separation to remove any residue from the preceding extraction stage.

DESCRIPTION OF PRESENTLY PREFERRED EMBODIMENTS

The selective recovery of certain nitrophenolic by-products, namely 2,4-DNP, picric acid or dinitrocresols, is illustrated utilizing dinitrocresol contaminated nitration waste water and non-cresol contaminated nitration waste water. The waste water utilized resulted from the production of nitrobenzene by an adiabatic nitration process. Ethylbenzene was utilized as the solvent in the extraction step.

It is noted that the isothermal or conventional nitration process does not produce picric acid, but does produce about 10% to 20% of the 2,6-dinitrophenol (2,6-DNP) isomer and some mono-nitrated phenols. The adiabatic process produces about 1% to 6% 2,6-DNP. This 2,6-DNP is generally present as the main impurity in the 2,4-DNP. Some isolation of the 2,6-DNP from the 2,4-DNP will occur when a preliminary extraction or precipitation is performed, such as used to remove cresols from the waste water as discussed above. Due to the low concentration of 2,6-DNP, i.e. less than about 500 parts per million (ppm), in the feed waste water stream as compared to the presence of about 5,000 ppm of 2,4-DNP and 5,000 ppm of picric acid, the solubility of the 2,6-DNP is not greatly exceeded when acidification is preformed. The fact that the solubility limit is not exceeded, serves to reduce the amount of 2,6-DNP which appears in the 2,4-DNP product. The normal amount of 2,6-DNP present in the 2,4-DNP is from about 1% to 4%.

Cresol Contaminated Water

Example 1

The first selective recovery was of dinitrocresols from nitration waste water. Nitrobenzene was essentially removed from the waste water by solvent extraction prior to being subjected to the process of the present invention.

The cresol concentration of the cresol contaminated nitration water utilized was initially 97.4 ppm. The pH of the nitration waste water was adjusted from an initial solution pH of 9.54 to a pH of 3.7 by adding sulfuric acid to the waste water. The water was then subjected to extraction. Following the extraction and recovery of the dinitrocresols, it was determined that the cresol concentration in the waste water had been reduced to 13.2 ppm. It is noted that when a pure dinitrocresol product is to be recovered, it preferably should be done from nitrotoluene waste water which has no dinitrophenols and a high concentration of dinitrocresols contained therein. The cresol concentration continued to decrease in the water layer as the acidity of the water was lowered. As the pH, however, reached the lower acid pH levels, a substantial amount of 2,4-DNP and/or picric acid was also extracted or pulled out of the water layer and accordingly, the purity level of the recovered cresol was lower.

Following the extraction of the dinitrocresols, the water layer was recovered so that 2,4-DNP and picric acid could then be selectively recovered from the same nitration water. The recovered water was subjected to a second pH adjustment by adding sulfuric acid in an amount sufficient to bring the pH of the water to a level of 2.5. The same nitration waste water after extraction of the pH adjusted water resulted in the reduction of the concentration of 2,4-DNP in the waste water from an initial concentration level of about 5,000 ppm to a concentration of less than about 100 ppm.

Thereafter, to selectively recover picric acid from the same nitration waste water, the water layer from the second extraction was recovered and its pH adjusted to a level of 0.6. Following extraction, the nitration waste water resulted in the reduction of the concentration of picric acid in the waste water from an initial concentration level of from about 5,000 ppm to a concentration of less than about 100 ppm.

Non-Cresol Contaminated Water

The non-cresol contaminated nitration waste water was essentially stripped of nitrobenzene by extraction before subjecting the waste water to the process of the present invention. Through the adjustment and control of the waste water pH, the concentration of 2,4-DNP and picric acid in the nitration waste water was reduced and a substantially pure form of 2,4-DNP and picric acid individually recovered. The recovery results following pH adjustment to varying levels and extraction are set forth below.

Example 2

Following adjustment of a nitration waste water's pH to 4.5 and extraction of the pH adjusted water, the concentration of 2,4-DNP in the nitration waste water was substantially reduced. Approximately 65% of the 2,4-DNP present in the waste water was removed from the water layer in a substantially pure form. To recover the remaining 2,4-DNP, i.e. approximately 35% of the original concentration, so that it would not be recovered with the picric acid, the pH is again lowered to a pH of about 2.0 to 1.6 and a second extraction performed. This second extraction removes the remaining 2,4-DNP thereby allowing for the subsequent extraction of picric acid in a relatively pure state. This method yields a picric acid product which is greater than 99% pure. The water's pH is adjusted to be from about 0.5 to 1.2 for the extraction of the picric acid. Preferably, the pH is adjusted to 1.0. This final extraction removes the picric acid from a concentration level of approximately 5,000 ppm down to a level of less than about 100 ppm.

Example 3

When the pH of a separate sample of nitration waste water was adjusted to 2.5 and the water subjected to extraction with the ratio of water to solvent being 5:1, the recovered solvent layer contained a composition of 99.8% 2,4-DNP and 0.2% picric acid.

Example 4

Extraction utilizing a 5:1 water to solvent ratio of another sample of nitration waste water following adjustment of the pH to 4.25 resulted in the recovery of a solvent layer containing 2,4-DNP at a high purity level. More specifically, analysis of the extract at a pH level of 4.25 following the evaporation of the solvent from the organic layer revealed a material composed of 97.3% 2,4-DNP and 2.7% picric acid.

For the analysis of the recovered material, the solvent wa removed from the organic extract layer using a roto-evaporator. Thereafter, the remaining solute was dissolved in deionized water. Analysis of the extracts was performed by liquid chromatography techniques using a 40% methanol/60% 4.5 pH water solvent system. The flow rate through the column was one ml/min. Detection was performed at 254 nm. An Alltech 5-micron, Econosphere C-18 column, 4.6 mm×25 cm was utilized with the liquid chromatography system. Injections were generally in microliters. Data reduction was done with a Spectraphysics Model 4270 integrator.

During the analysis of the picric acid recovered from the cresol contaminated water the concentrations initially appeared in an inconsistent manner. It was found that by treating the water samples with sulfamic acid prior to injection, that the sulfamic acid assisted in removing any nitrous acid present in the sample. The retention time of the nitrous acid is nearly identical to that of picric acid and thereby caused peak overlapping problems. After the samples were treated with sulfamic acid and subjected to liquid chromatography analysis, consistent and expected levels of picric acid were observed.

As will be apparent to one skilled in the art, various modifications can be made within the scope of the aforesaid description. Such modifications being within the ability of one skilled in the art form a part of the present invention and are embraced by the appended claims.

It is claimed:

1. A process for selectively recovering a nitrophenolic by-product in substantially pure form from nitration waste water, said nitrophenolic by-product being a member of the group consisting of 2,4-dinitrophenol and picric acid, comprising controlling the pH of said nitration waste water within the pH range of from about 4.5 to 0.5 through the addition of sulfuric acid to said nitration waste water to influence the solubility of said nitrophenolic by-product and separating said nitrophenolic by-product from said nitration waste water by solvent extraction.

2. A process according to claim 1 wherein said nitrophenolic by-product is 2,4-dinitrophenol and said pH is controlled in the range of from about 4.5 to 2.0.

3. A process according to claim 1 wherein said nitrophenolic by-product is picric acid and said pH is controlled in the range of from about 1.2 to 0.5.

4. A process according to claim 1 wherein said solvent utilized in said solvent extraction is a member selected from the group consisting of aromatic hydrocarbon solvents, non-aromatic solvents and chlorinated solvents.

5. A process according to claim 4 wherein said aromatic hydrocarbon solvents are selected from the group consisting of ethylbenzene, benzene and toluene.

6. A process for selectively recovering a nitrophenolic by-product in substantially pure form from nitration waste water, said nitrophenolic by-product being a member of the group consisting of 2,4-dinitrophenol and picric acid, comprising:
   (1) adding sulfuric acid to said nitration waste water in an amount sufficient to adjust the solution pH of said nitration waste water to a pH in the range of from about 4.5 to 0.5;
   (2) adding a solvent to said pH adjusted nitration waste water of step (1) and mixing said solvent and said water;
   (3) separating said mixed waste water of step (2) into an organic layer and a water layer; and
   (4) recovering said nitrophenolic by-product from said organic layer.

7. A process for selectively removing a nitrophenolic by-product from nitration waste water, said nitrophenolic by-product being a member of the group consisting of 2,4-dinitrophenol and picric acid, comprising:
   (1) adding sulfuric acid to said nitration waste water in an amount sufficient to adjust the solution pH of said nitration waste water to a pH in the range of from about 4.5 to 0.5;
   (2) adding a solvent to said pH adjusted nitration waste water of step (1) and mixing said solvent and said water; and
   (3) separating said mixed waste water of step (2) into an organic layer and a water layer,
wherein said nitrophenolic by-product is substantially removed from said water layer and is present in said organic layer of step (3).

8. A process according to claim 6 or claim 7 wherein said nitrophenolic by-product is 2,4-dinitrophenol and said pH is controlled in the range of from about 4.5 to 2.0.

9. A process according to claim 6 or claim 7 wherein said nitrophenolic by-product is picric acid and said pH is controlled in the range of from about 1.2 to 0.5.

10. A process according to claim 6 or 7 wherein said solvent is a member selected from the group consisting of aromatic hydrocarbon solvents, non-aromatic solvents and chlorinated solvents.

11. A process according to claim 10 wherein said aromatic hydrocarbon solvents are selected from the group consisting of toluene, benzene and ethylbenzene.

12. A process for selectively recovering a nitrophenolic by-product being from nitration waste water, said nitrophenolic by-product being a member of the group consisting of isometric dinitrocresols, 2,4-dinitrophenol, and picric acid comprising controlling the pH of said nitration waste water within the pH range of from about 4.5 to 0.5 through the addition of sulfuric acid to said nitration waste water to influence the solubility of said nitrophenolic by-product and separating said nitrophenolic by-product from said nitration waste water by solvent extraction, wherein said controlling of pH and said separating of said nitrophenolic by-product from said nitration waste water is carried out in such a manner that said dinitrocresols are recovered first, said 2,4-dinitrophenol is recovered second in substantially pure form and said picric acid is recovered third in substantially pure form.

13. A process according to claim 12 wherein when said nitrophenolic by-product is said isomeric dinitrocresols, said pH is controlled in the range of from about 4.5 to 3.7.

14. A process according to claim 12 wherein when said nitrophenolic by-product is 2,4-dinitrophenol, said pH is controlled in the range of from about 4.5 to 2.0.

15. A process according to claim 12 wherein when said nitrophenolic by-product is picric acid, said pH is controlled in the range of from about 1.2 to 0.5.

16. A process according to claim 12 wherein said solvent utilized in said solvent extraction is a member selected from the group consisting of aromatic hydrocarbon solvents, non-aromatic solvents and chlorinated solvents.

17. A process according to claim 16 wherein said aromatic hydrocarbon solvents are selected from the group consisting of ethylbenzene, benzene and toluene.

* * * * *